United States Patent [19]

Cree

[11] 4,311,853
[45] Jan. 19, 1982

[54] SELENIUM DERIVATIVES OF THYROXINE AND TRI-IODOTHYRONINE

[75] Inventor: Gavin M. Cree, Amersham, England

[73] Assignee: The Radiochemical Centre Limited, England

[21] Appl. No.: 116,777

[22] Filed: Jan. 30, 1980

[30] Foreign Application Priority Data

Feb. 6, 1979 [GB] United Kingdom ............... 04037/79

[51] Int. Cl.$^3$ .................. C07C 101/08; C07C 163/00
[52] U.S. Cl. ...................................... 562/447; 560/40; 564/165
[58] Field of Search ............................ 560/40, 37, 39; 562/447; 260/558 P, 558 R, 562 P, 562 A; 564/165

[56] References Cited

U.S. PATENT DOCUMENTS

| | | | |
|---|---|---|---|
| 2,579,668 | 12/1951 | Hems et al. ........................... | 560/40 |
| 3,930,017 | 12/1975 | Kummer et al. ...................... | 560/40 |
| 4,065,554 | 12/1977 | Tilly et al. ............................ | 560/37 |
| 4,139,605 | 2/1979 | Felder et al. ..................... | 260/558 P |

OTHER PUBLICATIONS

Paxton et al., Clin. Chem., 24/9, (1978), pp. 1534–1538.

*Primary Examiner*—Arthur P. Demers
*Attorney, Agent, or Firm*—Wenderoth, Lind & Ponack

[57] ABSTRACT

Novel Selenium derivatives of thyroxine and tri-iodothyronine have the formula:

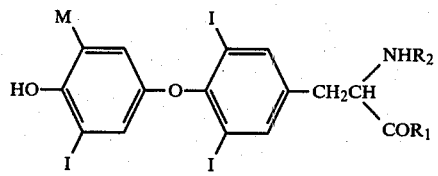

wherein M is I or H and either (a) $R_1$ is OH or a carboxyl protecting group and $R_2$ contains at least one Se, preferably $^{75}$Se, atom or (b) $R_2$ is H or an amino protecting group and $R_1$ contains at least one Se, preferably $^{75}$Se, atom.

The compounds are useful in dual isotope assays of thyroid function.

4 Claims, No Drawings

SELENIUM DERIVATIVES OF THYROXINE AND TRI-IODOTHYRONINE

This invention relates to selenium derivatives of thyroxine and tri-iodothyronine, and particularly to such selenium-75 derivatives, which are useful in dual isotope tests for thyroid function such as are described and claimed in our co-pending Application Ser. No. 116,776 filed on the same day as this one.

The principal thyroid hormones are thyroxine (T4) and tri-iodothyronine (T3) whose circulating levels in the blood regulate metabolic processes. Output of these hormones from the thyroid gland are controlled by the levels of thyroid stimulating hormone (TSH) secreted by the pituitary gland. The greater part of the T4 1 and T3 in circulation is protein bound, the most important carrier being thyroxine binding globulin (TBG). The free hormone concentrations have been shown to correlate well with thyroid status. An imbalance of the thyroid hormones leads to severe distress in patients but, with correct diagnosis, treatment is very effective. A catagorisation of patients into hypo-, eu-, and hyperthyroid states depends on the measurement of certain parameters in various combinations. More than one test is used because of the occurrence of borderline values, and the effects which age, pregnancy, disease, contraceptive and other drugs can have on measured values; reliance on a single test could result in mis-diagnosis.

The tests of thyroid function commonly used are estimations of total T4 and TSH or total T4 and T3, depending on the clinical situation. The most common means of assessing free T4 has been the Free Thyroxine Index (FTI), which is determined from measurements of total T4 and the spare binding capacity on TBG by a T3-uptake test. In those patients in whom measurements of binding proteins is indicated it may well be that the measurement of T3-uptake could be replaced by one of TBG, thus replacing the FTI value by a T4:TBG ratio.

In any clinical situation where it is required to measure two parameters it is obviously more economic if a dual parameter assay can be designed which requires only single operations for pipetting, incubation, centrifugation and counting instead of duplicate operations as would be the case for two independent assays. Dual parameter assays are made possible by the use of two isotopes differing in their gamma energies such that they may be counted simultaneously on a suitable gamma counter. Commercial dual isotope kits are now available which allow the simultaneous estimation of folate and vitamin $B_{12}$ by employing the isotopes iodine-125 and cobalt-57 respectively. In the thyroid field simultaneous determinations of T4 and T3 have been performed by utilising $^{125}$I-labelled thyroxine and $^{131}$I-labelled tri-iodothyronine (Hayes, S. P. and Goldie, D. J., Ann. Clin. Biochem., (1977) 14, 12–15; Brown, M. L. et al., J. Nucl. Med., (1977) 18, 300–304). The application of this latter dual isotope assay is, however, severely limited by the relatively short 8-day half-life of iodine-131.

The present invention overcomes this disadvantage by providing selenium-75 derivatives of T3 and T4. Selenium-75 is a gamma-emitting radionuclide with a half life of 118 days and peak emission energies of 121, 136, 265 and 379 KeV. In a dual assay kit, the use of selenium-75 instead of iodine-131 to label one of the components to be assayed confers the very significant advantage of a long assay kit shelf life as a result of the long half-life of selenium-75.

The selenium derivatives of T3 and T4 which constitute this invention have the formula set out below. In this formula, T3 has $R_1$ is hydroxyl and $R_2$ and M are both hydrogen; T4 has $R_1$ is hydroxyl, $R_2$ is hydrogen and M is iodine. The derivatives are:

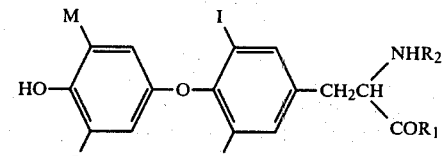

(a)

$R_1$ is OH or a carboxyl protecting group
$R_2$ is $-CO-CX_1X_2X_3$
at least one of $X_1$, $X_2$ and $X_3$ is $-A_p(SeQ)_q$
A is saturated alkylene of 1 to 4 carbon atoms
Q is alkyl or alkenyl of 1 to 6 carbon atoms, cycloalkyl, aryl or aralkyl,
p is 0 or 1
q is 1 or 2
one of $X_1$, $X_2$ and $X_3$ may be amino or $NHR_3$ where $R_3$ is H or an amino protecting group,
one or two of $X_1$, $X_2$ and $X_3$ may be H
M is H or I; or (b)

$R_2$ is H or an amino protecting group,
$R_1$ is $-NZ-CY_1Y_2Y_3$
at least one of $Y_1$, $Y_2$ and $Y_3$ is $-A-(SeQ)_q$ one of $Y_1$, $Y_2$ and $Y_3$ may be $-COOH$ or $COR_4$ where $R_4$ is OH or a carboxyl protecting group one or two of $Y_1$, $Y_2$ and $Y_3$ may be H
Z is H or $-A-(SeQ)_q$
A is saturated alkylene of 1 to 4 carbon atoms,
Q is alkyl or alkenyl of 1 to 6 carbon atoms, cycloalkyl, aryl or aralkyl,
Q is 1 or 2
M is H or I.

The following are examples of compounds that may be used to react with thyroxine, or a derivative thereof in which either the carboxyl or the amino group is protected, in this way:
$CH_3.Se\ CH_2.CH_2.NH_2$
$CH_3.Se\ CH_2.CH(NH_2).COOH$
$CH_3.Se\ CH_2.CH(Se\ CH_3).COOH$
$CH_3.C(CH_2.Se\ CH_3)_2.COOH$
$(CH_3.Se\ CH_2.\ CH_2)_2.NH$
$CH_3.SeCH_2CH_2COOH$
$CH_3C(CH_2SeCH_3)_2NH_2$
$C_6H_5.CH_2SeCH_2CH_2COOH$
$C_6H_5.CH_2SeCH_2CH_2NH_2$ The invention envisages both the inactive and the radioactive forms of the derivatives. The inactive forms are useful inter alia for determining the properties of the radioactive forms. In the radioactive forms, the selenium contains an artificially high proportion of Se-75, preferably such that the radioactive concentration of the derivative can be counted in a convenient time by a conventional gamma-radiation counter.

These derivatives may be prepared by methods known in the art. For example, isobutyl chloroformate is reacted with N-trifluoroacetyl T3 or T4 in the presence of a tertiary amine, the reaction being carried out at room temperature under anhydrous conditions in solvents such as dioxan and dimethylformamide in order to form the mixed anhydride. The mixed anhydride is subsequently reacted at room temperature in aqueous-organic media with the required selenoamine or selenoamino-acid or its ester, e.g. 2-methylseleno)-ethylamine or methylselenocysteine, to form an amide linkage between T3 or T4 and the seleno moiety. Instead of using isobutyl chloroformate to form the mixed anhydride the condensation of N-trifluoroacetyl T3 or T4 with either a selenoamine or selenoamino-acid may be effected in anhydrous solvents, e.g. dioxan or dimethylformamide, with reagents such as dicyclohexylcarbodiimide (DCC) or N-ethoxycarbonyl-2-ethoxy-dihydroquinoline (EEDQ). Alternatively, these procedures using DCC and EEDQ may be used to couple a T3 or T4 alkyl ester via its free amino group to a selenocarboxylic acid or a selenoamino-acid. Cleavage of protecting groups may be effected by known hydrolytic procedures. Final products are isolated by preparative thin-layer chromatography on silica gel.

The selenoamines, selenoamino-acids, and selenocarboxylic acids, used to synthesize the T3 or T4 derivatives, may be prepared by methods known in the art. For example, solutions of sodium alkyl, alkenyl, cycloalkyl, aryl or aralkyl selenides are prepared by reacting the appropriate halogen compounds with disodium diselenide in anhydrous liquid ammonia, and subsequently cleaving the organic diselenides so formed with metallic sodium. The sodium alkyl, alkenyl, cycloalkyl, aryl or aralkyl selenides are then further reacted in anhydrous liquid ammonia with suitable halogen derivatives of amines, amino-acids or carboxylic acids to form the required products.

The following Examples illustrate the invention.

EXAMPLE 1

(i) Preparation of N-trifluoroacetyl thyroxine

Thyroxine (240.6 mg; 0.310 mmoles) was suspended in trifluoroacetic anhydride (3 ml) and the mixture stirred under reflux for 4 hours. The trifluoroacetic anhydride was removed by evaporation in vacuo and the residue was dissolved in methanol (ca. 5 ml). On addition of water (20 ml) to the methanolic solution a precipitate formed, which was separated by centrifugation, washed with water (3×20 ml), and then dried in vacuo. Yield of N-trifluoroacetyl thyroxine, ca. 200 mg.

(ii) Preparation of 2-(methylseleno)-ethylamine-$^{75}$Se

Sodium selenite-$^{75}$Se (2.71 Ci; 21.7 Ci/matom) in acid solution was treated with sulphur dioxide to precipitate red selenium-$^{75}$Se, which after washing with water was transferred to a reaction tube and dried in vacuo. Yield, 2.48 Ci of red selenium-$^{75}$Se. The selenium-$^{75}$Se was suspended in anhydrous liquid ammonia and treated with sodium metal (3.1 mg; 0.135 matom) to produce a solution of disodium diselenide-$^{75}$Se. Excess methyl iodide (22.2 mg; 0.156 mmol) was added to form dimethyl diselenide-$^{75}$Se, which was cleaved by the further addition of sodium to form sodium methyl selenide-$^{75}$Se. 2-Bromoethylamine hydrobromide (22.8 mg; 0.111 mmol) was added to the reaction mixture which was then stirred until the ammonia had evaporated. The residue was held under vacuum for some time to remove volatile impurities, dissolved in water, and purified by preparative thin layer chromatography on silica gel (Eluent: butan-1-ol, acetic acid, water 60:15:25). The required zone was located by auto-radiography and the product recovered from the silica gel. Yield of 2-(methylseleno)-ethylamine-$^{75}$Se, 280 mCi.

(iii) Preparation of conjugate of thyroxine and 2-(methylseleno)-ethylamine-$^{75}$Se To N-trifluoroacetyl thyroxine (32.5 mg; $3.72 \times 10^{-2}$ mmol) dissolved in dry dimethylformamide (500 μl) was added dry triethylamine (5 μl; $3.59 \times 10^{-2}$ mmol) and isobutyl chloroformate (5 μl; $3.81 \times 10^{-2}$ mmol). After 3 minutes, 125 μl of this mixture was added to a solution of 2-(methylseleno)-ethylamine-$^{75}$Se (28.6 mCi; 21 Ci/mmol; $1.36 \times 10^{-3}$ mmol) in a mixture of dimethylformamide (1000 μl), water (500 μl) and triethylamine (10 μl). The reaction mixture was stirred at room temperature overnight, and after evaporation of volatile materials in vacuo the residue was treated with aqueous sodium hydroxide (1.2 ml of 1.16 N) at 70°–75° C. for 45 minutes. Water was evaporated and the lyophilized product was dissolved in methanol (500 μl) prior to purification by preparative thin layer chromatography on silica gel using chloroform, methanol, formic acid (80:15:5) as the developing eluent. Radioactive zones were located by autoradiography. The zone at $R_f$ ca. 0.5 was removed from the plate and the product eluted from the silica gel by successively washing with ammonium hydroxide solution in 50 percent aqueous ethanol (2 ml of N), and water (4×2 ml). The final solution was filtered to remove silica particles. Yield of $^{75}$Se-labelled thyroxine conjugate, 3.3 mCi. The purification process removes unreacted thyroxine. Accordingly, the specific activity of the product was 21 Ci/mmol.

EXAMPLE 2

(i) Preparation of Se-methyl-L-selenocysteine methyl ester-$^{75}$Se

Se-methyl-L-selenocysteine-$^{75}$Se (151 mg; 0.83 mmol; 26 mCi/mmol) was refluxed in methanolic hydrogen chloride for 30 minutes. Methanol was evaporated and the process repeated on the residue. After removal of methanol the lyophilized product was treated with dilute aqueous sodium bicarbonate, and the methyl ester was extracted from the mixture into chloroform. The chloroform solution was dried over anhydrous sodium sulphate and the solvent then evaporated to yield Se-methyl-L-selenocysteine methyl ester-$^{75}$Se as an oil.

(ii) Preparation of conjugate of thyroxine and Se-methyl-L-selenocysteine methyl ester-$^{75}$Se Se-methyl-L-selenocysteine methyl ester-$^{75}$Se (47 mg; 0.24 mmol; 19.4 mCi/mmol) was dissolved in dry dioxan (10 ml). 2 ml of this solution was added to a mixture of N-trifluoroacetyl thyroxine (33.5 mg; 0.0383 mmol) and dicyclohexylcarbodiimide (20 mg; 0.097 mmol) in dry dioxan (3 ml), and the reaction mixture stirred at room temperature for 24 hours. After removal of dioxan in vacuo the crude product was dissolved in methanol (500 μl) and purified by preparative thin layer chromatography on silica gel using ethyl acetate, methanol (4:1) as the developing eluent. The product was isolated from a UV absorbing radioactive zone near the solvent front. Yield, 147 μCi of $^{75}$Se-labelled thyroxine conjugate.

EXAMPLE 3

(i) Preparation of β-selenocyanatopropionic acid-$^{75}$Se

Red selenium-$^{75}$Se (366.7 mg; 4.46 matom; 0.526 mCi/matom) was dissolved in ca 3 ml of water containing potassium cyanide (301.2 mg; 4.63 mmol). After one hour the mixture was filtered to yield a solution of potassium selenocyanate-$^{75}$Se (2.07 mg; 3.93 mmol). β-propiolactone (3.09 mg; 4.27 mmol) was added to the solution, and the mixture stirred for one hour, acidified with hydrochloric acid, and allowed to stand overnight. It was then centrifuged and the supernatant was extracted with diethyl ether (2×25 ml). The ether was evaporated from the extract to yield β-selenocyanatopropionic acid-$^{75}$Se (254 mg; 1.43 mmol).

(ii) Preparation of benzylselenopropionic acid-$^{75}$Se

β-selenocyanatopropionic acid-$^{75}$Se (254 mg; 1.43 mmol) in ethanol (2 ml) was added dropwise with stirring to a mixture of sodium borohydride (191 mg; 5.50 mmol) and benzyl chloride (198 mg; 1.56 mmol) in 6 ml of ice-cold ethanol. After 1½ hours the reaction mixture was treated with 2 ml of acetone and a few drops of concentrated hydrochloric acid to destroy excess borohydride. Evaporation of solvents from the mixture yielded an oil, which was partitioned between ether and aqueous sodium hydrogen carbonate solution. The aqueous phase was acidified and re-extracted with ether. Evaporation of this ether phase yielded radiochemically pure benzylselenopropionic acid-$^{75}$Se.

(iii) Preparation of conjugate of thyroxine methyl ester and benzylselenopropionic acid-$^{75}$Se Thyroxine methyl ester (38.5 mg; 0.049 mmol), dicyclohexylcarbodiimide (22.8 mg; 0.11 mmol) and benzylselenopropionic acid-$^{75}$Se (20.8 mg; 0.086 mmol; 0.52 mCi/mmol) were stirred overnight in 10 ml of dry dioxan. The mixture was evaporated to dryness and the product examined by TLC in several solvent systems. In all cases a radioactive component was detected in addition to the unreacted thyroxine methyl ester and benzylselenopropionic acid-$^{75}$Se.

The product was redissolved in dioxan, the solution centrifuged, and the supernatant then applied to a preparative silica gel TLC plate. The plate was developed with chloroform, methanol (10:1) and the component of $R_f$ ca 0.9 was isolated by eluting the silica gel zone with ethanol. After evaporation of the ethanol the product was examined by infra red spectroscopy: the spectrum was consistent with the structure of T4 methyl ester/benzylselenopropionic acid conjugate. Yield 7.3 μCi.

EXAMPLE 4

(i) Preparation of N-trifluoroacetyl triiodothyronine

Triiodothyronine (456.7 mg) was suspended in trifluoroacetic anhydride (20 ml) and the mixture stirred under reflux for 4½ hours. The trifluoroacetic anhydride was removed by evaporation under reduced pressure. The residue was washed with water (3×25 ml) and then dried in vacuo. Yield of N-trifluoroacetyl triiodothyronine, 341.3 mg.

(ii) Preparation of conjugate of triiodothyronine and 2-(methylseleno)-ethylamine-$^{75}$Se The N-trifluoroacetyl triiodothyronine (24.0 mg; $3.21 \times 10^{-2}$ mmol) dissolved in dry dimethylformamide (500 μl) was added dry triethylamine (5 μl; $3.59 \times 10^2$ mmol) and isobutylchloroformate (5 μl; $3.81 \times 10^{-2}$ mmol). After 30 seconds 200 μl of this mixture was added to a solution of 2-(methylseleno)-ethylamine-$^{75}$Se (22.9 mCi; 17.4 Ci mmol; $1.31 \times 10^{-3}$ mmol) in a mixture of dimethylformamide (700 ml) and water (700 ml). The reaction mixture was diluted with 500 μl of dimethylformamide, stirred for one hour and allowed to stand at room temperature overnight. Volatile materials were removed from the mixture by evaporation in vacuo and the residue was treated with aqueous-ethanolic sodium hydroxide (1 ml of ethanol, 2 N aqueous sodium hydroxide (1:1) at 80° C. for 40 minutes. After the addition of 3 N hydrochloric acid (350 μl) solvents were evaporated in vacuo. The lyophilized product was dissolved in methanol (350 μl) and the solution applied to a preparative silica gel TLC plate which was developed with chloroform, methanol, formic acid (80:15:5). Radioactive zones were located by autoradiography. The zone at Rf ca 0.4 was removed from the plate and the product eluted from the silica gel with aqueous-ethanolic ammonium hydroxide. Yield of $^{75}$Se-labelled triiodothyronine conjugate, 126 μCi.

I claim:

1. Selenium derivatives of thyroxine and tri-iodothyronine having the formula:

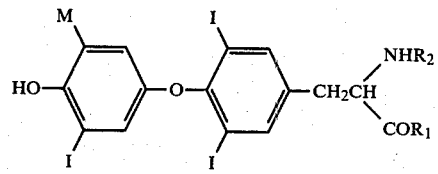

wherein either (a)

$R_1$ is OH $R_2$ is $-CO-CX_1X_2X_3$, at least one of $X_1$, $X_2$ and $X_3$ is $-A_p(SeQ)_q$, A is saturated alkylene of 1 of 4 carbon atoms, Q is alkyl or alkenyl of 1 to 6 carbon atoms, cycloalkyl, aryl or aralkyl, p is 0 or 1, q is 1 or 2, one of $X_1$, $X_2$ and $X_3$ may be amino and any other of $X_1$, $X_2$ or $X_3$ is H, and M is H or I; or (b)

$R_2$ is H, $R_1$ is $-NZ-CY_1Y_2Y_3$, at least one of $Y_1$, $Y_2$ and $Y_3$ is $-A-(SeQ)q$, one of $Y_1$, $Y_2$ and $Y_3$ may be $-COR_4$ where $R_4$ is OH, any other of $Y_1$, $Y_2$ and $Y_3$ may be H, Z is H or $-A-(SeQ)q$, A is saturated alkylene of 1 to 4 carbon atoms, Q is alkyl or alkenyl or 1 to 6 carbon atoms, cycloalkyl, aryl or aralkyl, q is 1 or 2, and M is H or I.

2. Derivatives according to claim 1, wherein, in alternative (a), $R_2$ is selected from $CH_3.SeCH_2.CH(NH_2).CO-$ $CH_3.SeCH_2.CH(SeCH_3).CO-$ $CH_3.C(CH_2.SeCH_3).CO-$ $CH_3.SeCH_2.CH_2.CO-$ $C_6H_5.CH_2.SeCH_2.CH_2.CO-$.

3. Derivatives according to claim 1, wherein, in alternative (b), $R_1$ is selected from
$CH_3.SeCH_2.CH_2.NH$—
$(CH_3.SeCH_2.CH_2)_2.N$—
$CH_3.C(CH_2.SeCH_3)_2.NH$—
$C_6H_5.CH_2.SeCH_2.CH_2.NH$—.

4. Derivatives according to claim 1 wherein the selenium comprises an artificially high proportion of selenium-75.

* * * * *